United States Patent [19]

Spinelli et al.

[11] Patent Number: 5,275,827
[45] Date of Patent: Jan. 4, 1994

[54] CIS-PLATINUM COMPLEXES WITH CHELATING AMINES AND SULPHINYL CARBOXYLATES

[75] Inventors: Silvano Spinelli; Alessandro Pasini; Carlo Bugatti; Mariella Valsecchi, all of Milan, Italy

[73] Assignee: Boehringer Mannheim Italia S.p.A., Milan, Italy

[21] Appl. No.: 916,136

[22] PCT Filed: Jan. 22, 1991

[86] PCT No.: PCT/EP91/00112
§ 371 Date: Jul. 30, 1992
§ 102(e) Date: Jul. 30, 1992

[87] PCT Pub. No.: WO91/11450
PCT Pub. Date: Aug. 8, 1991

[30] Foreign Application Priority Data

Jan. 31, 1990 [IT] Italy ............... 19210 A/90

[51] Int. Cl.$^5$ ............... A61K 33/24; A61K 31/28; C07F 15/00
[52] U.S. Cl. ............... 424/649; 514/492; 556/137
[58] Field of Search ............... 556/137; 514/492; 424/649

[56] References Cited

U.S. PATENT DOCUMENTS 4,849,437  7/1989  Di Domenico et al. ............ 514/365
4,871,528  10/1989  Tognella et al. ............ 424/10

FOREIGN PATENT DOCUMENTS 0328464  5/1989  European Pat. Off. .
8909598  10/1989  World Int. Prop. O. .

OTHER PUBLICATIONS

W. A. Freeman, J. Chem. Soc., Chem. Comm., No. 17, pp. 607-608 (1977).

*Primary Examiner*—José G. Dees
*Assistant Examiner*—Porfirio Nazario
*Attorney, Agent, or Firm*—Nikaido, Marmelstein, Murray & Oram

[57] ABSTRACT

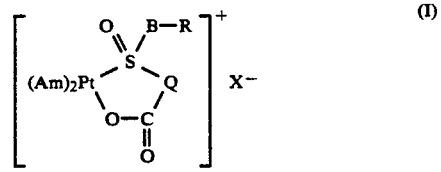

Platinum (II) complexes of formula (I) where: Am is a monodentate amine, or $(Am)_2$ is a bidentate amine, B represents a straight or branched alkyl residue or a single bond, R is selected from the group of hydrogen, $(C_3-C_8)$ cycloalkyl, phenyl or naphthyl which may be substituted by halogens (I, Br, Cl, F), trihalomethane, hydroxyl, $(C_1-C_4)$-alkoxyl, $(C_1-C_7)$-acylamino, $(C_1-C_7)$-sulphamido, allyl, phenoxyl, haloalkoxyl, nitro, cyano, azido, with condition that when R is hydrogen B is different from a single bond, Q is a residue of formula $-(CH_2)_{n1}-CR_aR_b-(CH_2)_{n2}-$, 1,2- or 2,3-naphthalene, benzo-1,3-dioxolan-5,6-diyl, substituted or unsubstituted 1,2-phenylene, $R_a$ and $R_b$ are selected independently of each other from the group of hydrogen, allyl, linear or branched $(C_1-C_8)$-alkyl, $-(CH_2)_pOH$, $-(CH_2CH_2O)_q-CH_3$, or taken together with the carbon atom to which they are bonded form a $(C_3-C_8)$ cycloalkyl, or heterocyclic tetrahydropyran-4,4-diyl, $n_1$ and $n_2$ are independently zero or the integer 1, p is an integer from 2 to 6, and q is an integer from 1-3, $X^-$ is a biocompatible anion such as chloride, bromide, iodide, nitrate, perchlorate, or one equivalent of sulphate or phosphate, or an anion of a monovalent $C_1-C_4$ organic acid such as acetate, propionate or chloroacetate, or of an aromatic acid such as benzoate, or of a heteroaromatic acid such as nicotinate are described. The compounds are useful as anti-tumor drugs.

9 Claims, No Drawings

CIS-PLATINUM COMPLEXES WITH CHELATING AMINES AND SULPHINYL CARBOXYLATES

This invention relates to platinum (II) complexes, useful as anti-tumour agents, a method for their preparation and the pharmaceutical compositions containing them.

More particularly the platinum (II) complexes according to the invention have the following formula I:

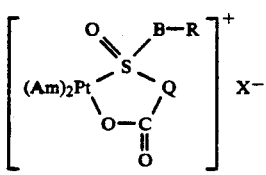

where:

Am is a monodentate amine, or $(Am)_2$ is a bidentate amine,

B is a single bond or a straight or branched saturated or unsaturated alkyl residue of 1-12 carbon atoms, R is selected from the group of hydrogen, $(C_3-C_8)$ cycloalkyl, phenyl or naphthyl which may be substituted by one or more halogen atoms or trihalomethane, hydroxyl, $(C_1-C_4)$-alkoxyl, $(C_1-C_7)$-acylamino, $(C_1-C_7)$-sulphamido, allyl, phenoxyl, $(C_1-C_7)$-haloalkoxyl, nitro, cyano or azido groups with the condition that when B is a single bond R can not be hydrogen, Q is a residue having the formula $-(CH_2)_{n1}-CR_aR_b-(CH_2)_{n2}-$, 1,2- or 2,3-naphthalene, benzo-1,3-dioxolan-5,6-diyl, 1,2- phenylene which may be substituted by one or more halogen atoms or trihalomethane, hydroxyl, $(C_1-C_4)$-alkoxyl, $(C_1-C_7)$-acylamino, $(C_1-C_7)$-alkyl or aryl-sulphamido, allyl, phenoxyl, $(C_1-C_7)$-haloalkoxyl, nitro, cyano or azido groups, $R_a$ and $R_b$ are independently hydrogen, allyl, linear or branched $(C_1-C_8)$-alkyl, a group having the formula $-(CH_2)_pOH$, $-(CH_2CH_2O)_q-CH_3$, or taken together with the carbon atom to which they are bonded form a $(C_3-C_8)$ cycloalkyl or tetrahydropyran-4,4'-diyl group, $n_1$ and $n_2$ are independently zero or the integer 1, p is an integer from 2 to 6 and q is an integer from 1 to 3, $X^-$ is a biocompatible anion.

Examples of biocompatible anions are chloride, bromide, iodide, nitrate, perchlorate, or one equivalent of sulphate or phosphate, or an anion of a monovalent $C_1-C_4$ organic acid such as acetate, propionate or chloroacetate, or of an aryl acid like p-toluate, benzoate and/or a heteroaromatic acid like nicotinate and the like.

The invention includes solvates, racemates, individual enantiomers, diastereoisomers and their mixtures of the compounds of formula I.

Examples of preferred monodentate amines are: $NH_3$, cyclopropylamine, cyclohexylamine, cyclopentylamine, n-propylamine, n-butylamine, isopropylamine.

Examples of preferred bidentate amines are: 1,2-diaminoethane, rac-(R,R)-, (S,S)- or meso-2,3-diaminobutane, trans-rac-, trans-(R,R)-, trans-(S,S)- or cis-meso-1,2-diaminocyclohexane, 1,1-bis-(aminomethyl) cyclohexane, rac,(+)a (−) 2-methyl-1,4-butanediacenine, cis- or trans-1-aminomethyl-2-aminocyclohexane and their enantiomers.

Preferred examples of the counteranion are: nitrate, ½ sulphate.

Examples of -B-R groups in which R is hydrogen are methyl, ethyl, propyl, isopropyl, n-butyl, isobutyl, t-butyl and allyl.

Examples of -B-R- groups in which B is a single bond are: phenyl, 4-chlorophenyl, 2-bromophenyl, 4-bromophenyl, 4-fluorophenyl, 4-trifluoromethylphenyl, 2-chlorophenyl, 2-fluorophenyl, 2,4-dichlorophenyl, 2,4-difluorophenyl, 4-methoxyphenyl, 2-methoxyphenyl, 4-acetylamminophenyl, 4-nitrophenyl, 4-cyanophenyl, 1- or 2-naphthyl.

Examples of -B-R- in which R is not hydrogen are benzyl and 4-methoxybenzyl.

Examples of Q groups are: methylene, 1,2-ethylene, 1,3-propylene, 1,2-phenylene, 1,1-cyclobutyl, 1,1-cyclopentyl, tetrahydropyran-4,4-diyl, benzo-1,3-dioxolan-5,6-diyl.

Examples of chiral sulphinylcarboxylic acids are: (R)- or (S)-(methylsulphinyl)acetic, (R)- or (S)-(phenylsulphinyl)acetic, (R)- or (S)-(benzylsulphinyl)acetic, (R)- or (S)-2-(methylsulphinyl)benzoic, (R)- or (S)-2-(phenylsulphinyl)benzoic, (R)- or (S)-3-(phenylsulphinyl)propionic, R or S 3-(phenysulphinyl)propionic acid.

Mono positively charged platinum complexes of formula cis-$[Pt(Am)_2(sulphoxide)Z]^+$ were reported in Chem. Biol. Interaction, 1975, pages 145-161 and in PCT/US/8901520 by Farrell; bis positively charged complexes of formula cis-$[Pt(Am)_2(sulphoxide)_2$ were disclosed in J. Chem. Soc. Chem. Comm. 1982, 331.

While bis(sulphoxide) complexes were substantially inactive in vivo as anti-tumour agent, due perhaps to the 2+ charge and lack of penetration into the cell, the chiral monocharged platinum amine sulphoxides disclosed in the above mentioned papers are described to be active in murine L1210 leukemia. In our hands all the above mentioned substances where poorly active in several experimental models of leukemias and solid tumour. In opposition the monochanged complexes of this invention have found to be endowed with marked anti-tumour activity, to be highly potent and characterized by high stability in aqueous and saline medium.

The process for the preparation of compounds according to this invention consists in reacting a platinum (II) complex of formula II

where:

Am and $(Am)_2$ are as previously described, and $T_1$ and $T_2$, which may be the same or different, are selected from the group of Cl, Br, I, $H_2O$, OH, $NO_3$, hydrogen sulphate or hydrogen carbonate, or, taken together, form a bidentate sulphate $(SO_4)$ or carbonate $(CO_3)$ group, with a compound of general formula III

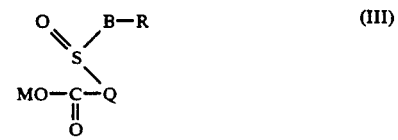

where B, R and Q are as previously defined and M represents a cation of an alkali metal, silver or one equivalent of a cation of an alkaline earth metal.

The reaction is generally performed by reaching compounds II and III in an equimolar ratio in solvents such as water, ($C_1$-$C_4$) alcohols, dimethylformamide, dimethylacetamide, N-methylpyrrolidone or their mixtures at temperatures between 0° and 80° C., preferably at 60° C.

If desired the reaction may also be performed by forming the silver salt of a sulphinylcarboxylic acid of formula (III) (M=Ag) "in situ" through reaction of the corresponding free acid with one equivalent of $Ag_2CO_3$, with the subsequent addition of an equimolar quantity of a compound of formula (II) in which $T_1$ and $T_2$ are Cl, I or Br and one equivalent of $AgNO_3$ or one equivalent of $Ag_2SO_4$ to yield a compound of formula I in which $X^-$ is $NO_3^-$ or $\frac{1}{2} SO_4^-$ respectively. Alternatively, if desired, the equivalent of $AgNO_3$ or $Ag_2SO_4$ may be generated in situ using 2 equivalents of $Ag_2CO_3$ and adding one equivalent of $HNO_3$ or $H_2SO_4$.

In this case the reaction is preferably performed in water, methanol or ethanol, or mixtures of these, at ambient temperature and in the dark, and is generally complete in 12 hours.

Compounds of formula (III) are generally prepared from the corresponding carboxylic acids of formula (IV)

$$\text{HO}-\underset{\underset{\text{O}}{\|}}{\text{C}}-(\text{Q})-\underset{\underset{\text{O}}{\|}}{\text{S}}-\text{B}-\text{R} \qquad (\text{IV})$$

through the action of the corresponding alkali, alkaline earth or silver hydroxides, bicarbonates or carbonates in accordance with known methods.

The carboxylic acids of general formula (IV) in which B, Q and R are as defined above are compounds which are known or which can be prepared by known methods, for example by the reaction of a halide or tosylate with an alkali or alkaline earth salt of a thiol to give a compound of formula (V)

R-B-S-Q-COOP   (V)

where B, R and Q are as previously defined and P is hydrogen or a $C_1$-$C_3$ alkyl such as methyl, ethyl or n-propyl. If P is not hydrogen, compounds (V) are saponified using conventional methods to yield the corresponding carboxylic acids (V), where P is hydrogen, which in turn are selectively oxidised by known methods ($NaIO_4$, equimolar hydrogen peroxide, microbiological oxidation, Sharpless oxidation) to yield the sulphinylcarboxylic acids (IV) which may be resolved if desired into their optical isomers by conventional methods such as the fractional crystallisation of salts with chiral amines and/or chromatographic separation on chiral phases.

Useful teachings for the preparation of alkylsulphinylacetic acids and their optical resolution are disclosed in U.S. Pat. No. 4,849,437 and in C.A. 42: 8786 d.

Useful teachings for the preparation of alkylphenylsulphinylpropionic acids, racemic alkylsulphinylbenzoic acids and their resolution into pure optical isomers are disclosed in: Canad. J. Chem. 51, 1704, (1973), J. Chem. Soc. (C): 731, (1969), J. Chem. Soc. Perkin (I): 282, (1975).

Complexes of formula II are well known and may be prepared for example as described in Indian J. Chem. 8, 193 (1970), Inorg. Chim. Acta 46, 15 (1980), Inorg. Chim. Acta 114, 127 (1986), Inorg. Chim. Acta 155, 267 (1989), Can. J. Chem. 1986, 64, 1984.

Useful teachings for the resolution of optical isomers of sulphinylcarboxylic acids can be found in J. Chem. Soc. Perkin (I), (1975), 282.

Generally, such isomers may be obtained by fractional crystallisation of the diastereoisomeric mixture of the salts of racemic sulphinylcarboxylic acids with an optically active base such as for example brucine, cinchonine, ephedrine, phenylethylamine and the like.

The compounds according to the invention are generally very soluble in water, physiological saline and solvents which are miscible with water.

The compounds according to the invention not only have marked anti-tumour activity but also have low toxicity and therefore their therapeutic index is particularly favourable.

The high water-solubility of the platinum complexes according to this invention also facilitates the preparation of parenteral and oral pharmaceutical forms.

When administered to men and animals bearing tumours which can be cured by platinum complexes, in variable doses between 1 mg and 1.2 g per square meter of body surface, the compounds of formula I can induce regression of the above-mentioned tumoral forms.

The effective dose for compounds according to the invention may be determined by an expert clinician using conventional known methods. The correlation between the doses used with animals of various species and sizes and humans (on the basis of mg/m² of body surface area) has been described by Freirech, E. J. et al., Quantitative Comparison of Toxicity of Anticancer Agents in Mouse, Rat, Hamster, Dog, Monkey and Man. Cancer Chemother. Rep. 50 no. 4, 219-244, May 1966.

Usually, however, will be administered to patients doses ranging from 1 and 1200 mg/kg of the complex, in a dosage regimen which is dependent on a number of factors which are well known to clinicians skilled in the art.

Sometimes it may be advantageous to administer the platinum complex according to this invention with one or more agents which potentiate its anti-tumour activity or which mitigate undesirable collateral effects due to the platinum complex.

For example platinum complexes according to this invention may be administered together with reduced glutathione, as described in GB 2174905 and U.S. Pat. No. 4,871,528.

It is accepted that some of the platinum complexes having the formula described above may have such high toxicity, or such an unfavourable therapeutic index, that they are not suitable for anti-tumour treatment in patients. However these parameters may rapidly be determined by conventional pharmacological screening tests such as, for example, those using L-1210 mouse laukaemia cells implanted in mice. Complexes which prove to be toxic will of course be avoided.

The tumours in patients which can be treated using platinum complexes according to this invention are those tumours which are known to be susceptible to treatment with platinum complexes. It is known that cis-platinum and carboplatinum have already been used clinically for the treatment of tumours of the testicles, ovaries, bladder, head and neck. It is also known that these drugs have demonstrated activity, although limited activity, against tumours of the lungs (not microcytoma), osteogenic sarcoma, Hodgkin's lymphoma, melanoma and tumours of the breast.

Cis-platinum is active in squamous cell carcinoma of the head and neck, in anaplastic tumour of the lungs (in combination with VP-16 and/or Vinca alkaloids), in adenocarcinoma of the stomach, in carcinoma of the oesophagus, in adenocarcinoma of the prostate, in osteogenic sarcoma, in sarcoma of the bone and soft tissue, in non-Hodgkin's lymphoma, in adenocarcinoma of the breast, in tumours of the brain, in tumours of the endometrium and in tumours of the thyroid. All these tumours are sensitive to treatment with the platinum complexes according to this invention. The complexes according to this invention are also active against certain tumours which are resistant to cis-platinum, as has been demonstrated by investigations on animals performed using the compounds according to the invention.

The treatment regimen may be varied as necessary as is well known to any medical expert in the treatment of tumour forms, in relation to the type of tumour being treated and the condition of the patient.

The compounds according to the invention are preferably administered as sterile aqueous solutions. The solutions are preferably administered intravenously or intra-arterially, although other forms of administration may be indicated in special cases.

The pharmaceutical forms which can be used for parenteral administration include sterile aqueous solutions or sterile powders for the preparation of solutions as required, and oil-based preparations for intramuscular or intraperitoneal administration.

Other useful pharmaceutical forms may be syrups or similar liquid forms, as well as solid forms such as tablets, capsules or the like.

The examples below will serve to provide a better illustration of the invention and do not in any way constitute a limitation thereupon.

EXAMPLE 1

A 36% solution of hydrogen peroxide (19.84 ml) was slowly dropped with stirring into a solution of methylmercaptoacetic acid (17.94 ml) in ethanol (55 ml, 95%) cooled to 0° C. After the addition is completed (30 minutes), the reaction mixture was left to react for 1 hour at 30–35x. 0.2 g of 10% Pd on carbon were then added with stirring. The resulting suspension was then stirred for a further 1 hour, filtered and concentrated to small volume. The resulting solution was diluted with anhydrous ethyl alcohol and reconcentrated under vacuum; the above procedure was repeated several times in order to eliminate traces of water. Acetone (25 ml) was finally added to the oily residue and the resulting solution was cooled at 0° overnight.

The obtained white precipitate was filtered and dried under vacuum. 17.4 g of ($\pm$)methylsulphinylacetic acid (m.p. 84.5°–85.5° C.) were obtained.

The following sulphinylcarboxylic acids were obtained using a similar procedure:
ethylsulphinylacetic acid (m.p. 57°–6° C.)
n-propylsulphinylacetic acid (m.p. 75°–6° C.)
isopropylsulphinylacetic acid (m.p. 80°–1° C.)
n-butylsulphinylacetic acid
t-butylsulphinylacetic acid
benzylsulphinylacetic acid
phenylsulphinylacetic acid
allylsulphinylacetic acid
3-(methylsulphinyl)propionic acid
3-(ethylsulphinyl)propionic acid
3-(n-propylsulphinyl)propionic acid
3-(isopropylsulphinyl)propionic acid
3-(n-butylsulphinyl)propionic acid
3-(t-butylsulphinyl)propionic acid
3-(benzylsulphinyl)propionic acid
3-(phenylsulphinyl)propionic acid
3-(allylsulphinyl)propionic acid
1-(methylsulphinyl)cyclobutane-1-carboxylic acid

EXAMPLE 2

Methylsulphinylacetic acid (0.0618 g; 0.50 mmol) and 0.1N KOH 4.9 ml were added to a solution of 0.185 g of 1,2-diaminoethanedinitrate platinum (II) (0.49 mmol) in 10 ml of deionised water. The resulting solution was heated to 60° C. for 5 hours, cooled and concentrated to 5 ml, yielding 153 mg of 1,2-diaminoethanemethylsulphinylacetatoplatinum (II) nitrate (yield 70%). Elemental analysis: % found: C 13.65, H 3.05, N 9.67, Pt 43.29. % calculated for $C_5H_{13}N_3O_6SPt$: C 13.70, H 2.97, N 9.59, Pt 44.53.

$^1$H NMR($D_2O$, ref TMS): $\delta=2.85$ (4H, m, $J_{Pt-H}$45.5 Hz, ethylenediamine), $\delta=3.76$ (3H, s, $J_{Pt-H}$45.5 Hz, methylsulphinyl). The protons of the methylene group exchange rapidly with D20 and are not visible.

Infrared spectrum: 1620 cm$^{-1}$ coordinated carboxyl, 1380 cm$^{-1}$ nitrate ion, 1100 cm$^{-1}$ sulphoxide coordinated via sulphur (free sulphoxide 1000 cm$^{-1}$).

EXAMPLE 3

When cis-diaminedinitratoplatinum(II), trans-rac-1,2-diamino-cyclohexanedinitratoplatinum(II), trans-(R,R)-1,2-diaminecyclohexanedinitratoplatinum(II), trans-(S,S)-1,2-diaminecyclohexane-dinitratoplatinum (II), cis-meso-1,2-diaminecyclohexanedinitrato-platinum(II), meso-2,3-diaminebutanedinitratoplatinum(II) and cis-1,1(diaminemethyl)cyclohexanenitratoplatinum (II) were reacted with methylsulphinylacetic acid in accordance with the procedure described in the previous examples, the following compounds were obtained: cis-diaminemethylsulphinylacetatoplatinum(II) nitrate, trans-rac-1,2-diaminecyclohexanemethylsulphinylacetatoplatinum(II) nitrate, trans-(R,R)-1,2-diaminecyclohexanemethylsulphinylacetatoplatinum-(II) nitrate, trans-(S,S)-1,2-diaminecyclohexanemethylsulphinylacetatoplatinum(II) nitrate, cis-meso-1,2-diaminecyclohexanemethylsulphinylacetatoplatinum-(II)nitrate, meso-2,3-diaminebutanemethylsulphinylacetato-platinum(II) nitrate, cis 1,1(diaminemethyl)cyclohexanemethylsulphinylacetatoplatinum(II) nitrate.

EXAMPLE 4

A solution of trans-rac-1,2-diaminecyclohexanedinitratoplatinum(II) (0.241 g, 0.56 mmol) in 10 ml of deionised water was treated with 0.104 g (0.56 mmol) of ($\pm$) 2-(methylsulphinyl)benzoic acid and 5.6 ml of 0.1N KOH. The suspension obtained was warmed at 60° C. for 7 hours. By cooling the resulting solution 0.151 g (yield 48%) of trans-rac-1,2-diammino-cyclohexane-2-(methylsulphinyl)benzoatoplatinum(II) nitrate are obtained.

Analysis: % found: C 30.01, H 3.91, N 7.49, Pt 34.73; % calculated for $C_{14}H_{21}N_3O_6SPt$: C 30.31, H 3.79, N 7.58, Pt 35.21.

$^1$H NMR ($D_2O$, ref TMS) so $\delta=1-2.8$ (10H, mt, diaminocyclohexane), $\delta=3.76$ and 3.68 (3H, two singlets, diastereoisomeric mixture $J_{Pt-H}$21.9 Hz), δ=7.8–8.3 (4H, mt, aromatic ring).

Infrared spectrum (KBr pellets): 1618 cm$^{-1}$ coordinated carboxyl, 1380 cm$^{-1}$ nitrate ion, 1136 cm$^{-1}$ sulphoxide coordinated via sulphur (free ligand: 950 cm$^{-1}$).

EXAMPLE 5

When cis-diaminedinitratoplatinum(II), 1,2-diaminoethanedinitratoplatinum(II), trans-(R,R)-1,2-diaminecyclohexanedinitratoplatinum(II), trans-(S,S)-1,2-diaminecyclohexanedinitratoplatinum(II), cis-meso-1,2-diaminecyclohexanedinitratoplatinum(II), 1,1-bis-(aminomethyl)cyclohexanedinitratoplatinum(II) are reacted with 2-(methylsulphinyl)benzoic acid as in example 3 the following compounds are obtained: cis-diamine-2-(methylsulphinyl)benzoatoplatinum(II)nitrate, 1,2-diaminaethane-2-(methylsulphinyl)benzoatoplatinum(II) nitrate, trans-(R,R)-1,2-diaminocyclohexane-2-(methylsulphinyl)benzoatoplatinum(II) nitrate, trans-(S,S)-1,2-diaminocyclohexane-2-(methyl-sulphinyl)benzoatoplatinum(II) nitrate, cis-meso-1,2-diaminocyclo-hexane-2-(methylsulphinyl)benzoatoplatinum(II) nitrate, 1,1-bis(aminomethyl)cyclohexane-2(methylsulphinyl)benzoatoplatinum(II) nitrate.

EXAMPLE 6

Silver carbonate (1.94 g) was added to a solution of (−)-3-phenyl-sulphinylpropionic acid (1.4 g) in water (70 ml). The resulting suspension was stirred at room temperature away from the light for 30 minutes and then filtered. The filtrate was added to a suspension of cis-1,1-bis(aminomethyl)cyclohexane-dichloroplatinum(II) (2.86 g) in 10 ml of water, and silver nitrate (1.19 g) in 5 ml of water was added to this mixture. The resulting suspension was stirred away from the light for 12 hours, and then filtered. The clear filtrate was evaporated to dryness under vacuum. The residue was then taken up in MeOH and diluted with an equal volume of ethyl ether and cooled to 0° C. The white crystalline precipitate formed overnight, was filtered off and washed with ethyl ether giving 1.7 g of 1,1-bis(amminomethyl)cyclohexane-3-phenylsulphinylpropionatoplatinum(II).

EXAMPLE 7

When 1,1-bis(aminomethyl)cyclohexanedichloroplatinum(II) was reacted in accordance with the procedures described in examples 2 or 6 with 3-(methylsulphinyl)propionic, 3-(ethylsulphinyl)propionic, 3-(n-propylsulphinyl)propionic, 3-(isopropylsulphinyl)propionic, 3-(n-butylsulphinyl)propionic, 3-(t-butylsulphinyl)propionic, 3-(benzylsulphinyl)propionic, and 3-(allylsulphinyl)propionic acids (prepared in accordance with the method in example 1) the following complexes were obtained:

1,1-bis(aminomethyl)cyclohexane-3-(methylsulphinyl)propionatoplatinum(II) nitrate, 1,1-bis-(aminomethyl)cyclohexane-3-(ethylsulphinyl)propionato-platinum(II) nitrate, 1,1-bis(aminomethyl)cyclohexane-3-(n-propylsulphinyl)propionatoplatinum(II) nitrate, 1,1-bis(aminomethyl)cyclohexane-3-(isopropylsulphinyl)propionatoplatinum(II) nitrate, 1,1-bis-(aminomethyl)cyclohexane-3-(n-butylsulphinyl)propionatoplatinum(II) nitrate, 1,1-bis-(aminomethyl)cyclohexane-3-(t-butylsulphinyl)propionatoplatinum(II) nitrate, 1,1-bis(aminomethyl)cyclohexane-3-(benzylsulphinyl)propionatoplatinum(II) nitrate, 1,1-bis-(aminomethyl)cyclohexane-3-(allylsulphinyl)propionato-platinum(II) nitrate.

EXAMPLE 8

When 1,1-bis(aminomethyl)cyclohexanedinitratoplatinum(II) was reacted in accordance with the procedures described in examples 2 or 6 with ethylsulphinylacetic, n-propylsulphinylacetic, isopropylsulphinylacetic, n-butylsulphinylacetic, t-butylsulphinylacetic, benzylsulphinylacetic, phenylsulphinylacetic and allylsulphinylacetic acids the following compounds were obtained: 1,1-bis(aminomethyl)cyclohexaneethylsulphinylacetatoplatinum(II) nitrate, 1,1-bis(aminomethyl)cyclohexane-n-propylsulphinylacetato-platinum(II) nitrate, 1,1-bis-(aminomethyl)cyclohexaneisopropylsulphinylacetatoplatinum(II) nitrate, 1,1-bis-(aminomethyl)cyclohexane-n-butylsulphinylacetatoplatinum(II) nitrate, 1,1-bis(aminomethyl)cyclohexane-t-butylsulphinylacetatoplatinum(II) nitrate, 1,1-bis(aminomethyl)cyclohexanebenzylsulphinylacetatoplatinum(II) nitrate, 1,1-bis(aminomethyl)cyclohexanephenylsulphinylacetatoplatinum(II) nitrate, 1,1-bis-(aminomethyl)cyclohexaneallylsulphinylacetatoplatinum(II) nitrate.

EXAMPLE 9

When trans-(R,R)-1,2-diaminocyclohexanedinitratoplatinum(II), trans-(S,S)-1,2-diamminocyclohexanedinitratoplatinum(II) are reacted in accordance with the procedures in examples 2 or 6 with (−)-2-ethylsulphinylbenzoic, (+)-2-ethylsulphinylbenzoic, (+)-3-phenylsulphinylpropionic and 1-(methylsulphinyl)cyclobutane-1-carboxylic acids the following compounds are obtained:

trans-(R,R)-1,2-diaminocyclohexane(−)-2-(ethylsulphinyl)benzoatoplatinum(II) nitrate, trans-(S,S)-1,2-diaminocyclohexane(−)-2-(ethylsulphinyl)benzoatoplatinum (II) nitrate, trans-(R,R)-1,2-diaminocyclohexane-(+)-2-(ethylsulphinyl)benzoatoplatinum(II) nitrate, trans-(R,R)-1,2-diaminocyclohexane-(+)-3-(phenylsulphinyl)propionatoplatinum(II) nitrate, trans-(R,R)-1,2-diaminocyclohexane-1-(methylsulphinyl)cyclobutane-1-carboxylatoplatinum(II)nitrate.

EXAMPLE 10

When trans-(R,R)-1,2-diaminocyclohexanedichloroplatinum(II) or trans-(S,S)-1,2-diaminocyclohexanedichloroplatinum(II) or 1,1-bis(aminomethylcyclohexane)dichloroplatinum(II) are reacted in accordance with the procedure described in example 6 with (−)-2-methylsulphinylbenzoic and (+)-2-methylsulphinylbenzoic acids the following complexes are obtained:

trans-(R,R)-1,2-diaminocyclohexane(−)-2-(methylsulphinyl)benzoatoplatinum(II) nitrate 1H NMR (D20, ref TMS) δ=8.15–8.25 (m, 1H), δ=7.80–8.05 (m, 3H aromatic), δ=1.1–1.5 (m, 4H), δ=1.5–1.7 (m, 2H), δ=2.0–2.2 (m, 2H), δ=2.45–2.75 (m, 2H), δ=3.65 (t, $J_{Pt-H}$=10.17 Hz, 3H), CH$_3$SO.

$[α]_D^{20}$ (c=0.2 in H$_2$O): −13°.34

Trans-(R,R)-1,2-diaminocyclohexane(+)-2-(methylsulphinyl)benzoatoplatinum(II)

$^1$H NMR (D20, ref TMS) δ=8.15–8.25 (m, 1H), δ=7.78–8.02 (m, 3H aromatic), δ=1.05–1.5 (m, 4H), δ=1.5–1.75 (m, 2H), δ=2.0–2.18 (m, 2H), δ=2.48–2.78 (m, 2H), δ=3.65 (t, $J_{Pt-H}$=10.17 Hz, 3H), CH$_3$SO.

$[α]_D^{20}$ (c=0.2 in H$_2$O): +138°

1,1-bis(aminomethyl)cyclohexane(−)-2-(methylsulphinyl)-benzoato-platinum(II) nitrate $^1$H NMR (D20, reference TMS) δ=8.15-8.25 (m, 1H), δ=7.80-8.05 (m, 3H aromatic), δ=1.25-1.60 (m, 10H), δ=2.30-2.75 (m, 4H) CH2NH2, δ=3.62 (t, JPt-H=10.17 Hz, 3H) CH3SO.

[α]$_D^{20}$ (c=0.2 in H$_2$O): −72°.5

Trans-(S,S)-1,2-diaminocyclohexane (+)-2-(methylsulphinyl)benzoatoplatinum (II) nitrate

[α]$_D^{20}$ (c=0.2 in H$_2$ O): −7°.89

Trans-(S,S)-1,2-diaminocyclohexane(−)-2-(methylsulphinyl)benzoatoplatinum(II) nitrate

[α]$_D^{20}$ (c=0.2 in H$_2$ O): −111°. 85

EXAMPLE 11

When cis-(amine) (cyclohexylamine)dichloroplatinum (II) or cis-(amine) (cyclopentylamine)dichloroplatinum (II) are reacted in accordance with the procedure described in example 6 with (−)2-methylsulphinylbenzoic acid and (+)2-methylsulphinylbenzoic acid the following complexes are obtained:

cis-(amine) (cyclohexylamine) (−)2-methylsulphynilbenzoatoplatinum(II) nitrate cis-(amine) (cyclopentylamine) (+)2-methylsulphynilbenzoatoplatinum(II) nitrate.

We claim:

1. A complex of platinum (II) of formula I

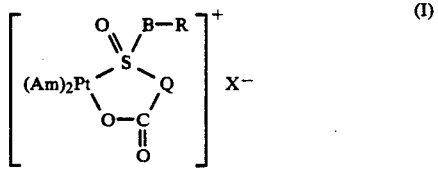

where:
Am is a monodentate amine, or
(Am)2 is a bidentate amine,
B is a single bond or a straight or branched saturated or unsaturated alkyl residue of 1-12 carbon atoms,
R is selected from the group of hydrogen, (C$_3$-C$_8$) cycloalkyl, phenyl or naphthyl which may or may not be substituted by one or more halogen atoms or trihalomethane, hydroxyl, (C$_1$-C$_4$)-alkoxyl, (C$_1$-C$_7$)-acylammino, (C$_1$-C$_7$)-sulphamido, allyl, phenoxyl, (C$_1$-C$_7$) -haloalkoxyl, nitro, cyano or azido groups with the condition that when B is a single bond R can not be hydrogen,
Q is a residue having the formula —(CH$_2$)$_{n1}$—CR$_a$R$_b$—(CH$_2$)$_{n2}$—, 1,2- or 2,3-naphthalene, benzo-1,3-dioxolan-5,6-diyl, 1,2-phenylene which may or may not be substituted by one or more atoms of halogen or trihalomethane, hydroxyl, (C$_1$-C$_4$) alkoxyl, (C$_1$-C$_7$)-acylamino, (C$_1$-C$_7$)-alkyl or aryl-sulphamino, allyl, phenoxyl, (C$_1$-C$_7$)-haloalkoxyl, nitro, cyano or azido groups,
Ra and Rb are independently hydrogen, allyl, straight or branched (C$_1$-C$_8$) alkyl, a group having the formula —(CH$_2$)$_p$OH, —(CH$_2$CH$_2$O)$_q$—CH$_3$, or together with the carbon atom to which they are bonded form a (C$_3$-C$_8$)-cycloalkyl or tetrahydropyran-4,4-diyl group,
n$_1$ and n$_2$ are independently zero or the integer 1, p is an integer from 2 to 6 and q is an integer from 1 to 3,
X$^-$ is a biocompatible anion.

2. The complex according to claim 1 in which mono- or bidentate amines are selected from NH$_3$, cyclopropylamine, cyclohexylamine, cyclopentylamine, n-propylamine, n-butylamine, isopropylamine, 1,2-diaminoethane, rac-, (R,R)-, (S,S)- or meso-2,3-diaminobutane, trans-rac-, trans-(R,R)-, trans-(S,S)- or cis-meso-1,2-diaminocyclohexane, 1,1-bis(aminomethyl)cyclohexane, cis or trans 1-aminomethyl-2-aminocyclohexane and its enantiomers, rac, (+) or (−) 2-methyl-1,4-butanediamine.

3. The complex according to claim 1 in which Q is selected from methylene, 1,2-ethylene, 1,3-propylene, 1,2-phenylene, 1,1-cyclobutyl, 1,1-cyclopentyl, tetrahydropyran-4,4-diyl, benzo-1,3-dioxolan-5,6-diyl.

4. The complex according to claim 1 in which -B-R- represents methyl, ethyl, propyl, isopropyl, n-butyl, isobutyl, t-butyl allyl.

5. The complex according to claim 1 in which B is a single bond and R is selected from phenyl, 4-chlorophenyl, 4-bromophenyl, 2-bromophenyl, 4-fluorophenyl, 4-trifluoromethylphenyl, 2-chlorophenyl, 2-fluorophenyl, 2,4-dichlorophenyl, 2,4-difluorophenyl, 4-methoxyphenyl, 2-methoxyphenyl, 4-acetylamminophenyl, 4-nitrophenyl, 4-cyanophenyl, 1- or 2naphthyl.

6. A method of preparing an anti-tumor medicament, comprising adding at least one compound according to claim 1 to a suitable vehicle.

7. A method of treating a patient suffering from a platinum complex-treatable tumor, the method comprising administering to said patient a tumor regression effective amount of a compound according to claim 1.

8. A process for the preparation of compounds according to this invention which consists in reacting a platinum (II) complex of formula II

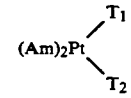

where: Am and (Am)$_2$ are as previously described as in claim 1 and T$_1$ and T$_2$, which may be the same or different, are selected from the group Cl, Br, I, H$_2$O, OH, NO$_3$, bisulphate, bicarbonate or, taken together, form a bidentate sulphate (SO$_4$) or carbonate (CO$_3$) group, with a compound of general formula III

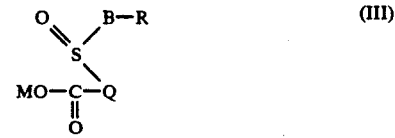

where B, R and Q are as defined previously as in claim 1 and M represents a cation of an alkali metal, silver, or one equivalent of an alkaline earth metal cation.

9. A pharmaceutical composition containing a complex according to claim 1 the active ingredient in a mixture with a suitable vehicle.

* * * * *